US005623200A

United States Patent [19]
Ogino

[11] Patent Number: 5,623,200
[45] Date of Patent: Apr. 22, 1997

[54] PARTICLE MEASURING APPARATUS AND PARTICLE MEASURING METHOD BY THE APPARATUS

[75] Inventor: Shinichi Ogino, Kobe, Japan

[73] Assignee: Toa Medical Electronics Co., Ltd., Hyogo-ken, Japan

[21] Appl. No.: 436,568

[22] Filed: May 8, 1995

[30]  Foreign Application Priority Data

May 9, 1994  [JP]  Japan .................................... 6-095206

[51] Int. Cl.⁶ ................................................. G01N 15/02
[52] U.S. Cl. ......................... 324/71.4; 73/865.5; 324/699
[58] Field of Search ................................ 324/699, 71.4; 73/865.5

[56]  References Cited

U.S. PATENT DOCUMENTS

| | | |
|---|---|---|
| 3,783,376 | 1/1974 | Doniguian . |
| 3,958,177 | 5/1976 | Reeves et al. . |
| 4,471,297 | 9/1984 | Berg ..................... 324/71.4 X |
| 4,760,328 | 7/1988 | Groves ..................... 324/71.4 |
| 4,901,024 | 2/1990 | Miyake et al. ........... 324/71.4 X |
| 5,376,878 | 12/1994 | Fisher ..................... 324/71.4 |

FOREIGN PATENT DOCUMENTS

| | | | |
|---|---|---|---|
| 2145531 | 3/1973 | Germany ............................... 324/71.4 |
| 611319 | 6/1978 | U.S.S.R. ................................ 324/71.4 |
| 907028 | 9/1962 | United Kingdom .................. 324/71.4 |
| 2232769 | 12/1990 | United Kingdom . |

Primary Examiner—Thomas P. Noland

[57]  ABSTRACT

Particle measuring apparatus 1 comprising slide plate 3 set between tanks 2a and 2b and having through-holes 8 to 11 passing through slide plate 3 and a pair of electrodes 4a and 4b, wherein through-holes 8 to 11 on slide plate 3 are formed by a group of through-holes with different diameters. When one of the through-holes 8 to 11 is brought to a position corresponding to connective holes 2c and 2d by driving unit 7, particle distribution is measured and analyzed in accordance with the electrical impedance when a sample suspension passes through the through-hole.

12 Claims, 11 Drawing Sheets

PARTICLE MEASURING APPARATUS AND PARTICLE MEASURING METHOD BY THE APPARATUS

BACKGROUND OF THE INVENTION

1. Field of the Invention

The present invention relates to a particle measuring apparatus and a particle measuring method by the apparatus, particularly to a particle measuring apparatus and a particle measuring method by the apparatus for measuring blood cells, or particles of latex or cement powder using the electrical-impedance-change detection method for measuring particles in a sample suspension in accordance with a change of electrical impedance by passing the sample suspension through a through-hole.

2. Prior Arts

To measure the particle-diameter distribution of blood cells in blood or industrial particles of cement powder and latex, particle-diameter distribution measurement using the electrical-resistance-change detection method has been performed. In the case of this measurement, a slide plate having a through-hole through which a sample suspension can pass is arranged at a connective portion of a sample vessel to measure and analyze particles passing through the through-hole as disclosed for example, in U.S. Pat. No. 3,783,376. A particle-diameter distribution is obtained by measuring the number of particles by the number of signal pulses generated when particles pass through the through-hole and the volume of a particle by the pulse height. In the case of the above disclosed example, one through-hole is bored on one slide plate.

In the case of the electrical-resistance-change detection method, because a change of the electrical resistance of a sample suspension when a particle passes through the sample suspension is linearly measured, the intensity of signal to be penetrated is proportional to the volume of the particle. However, measurable particle diameter is limited by the through-hole diameter. For example, when the diameter of a particle decreases to 1/30 the through-hole diameter or less, it is difficult to separate a particle signal from noise. On the contrary, when the particle is too large, the through-hole is clogged and thereby the particle is prevented from passing through the through-hole.

Thus, accurate measurement cannot be made. Therefore, to measure samples having a wide particle-distribution, it is necessary to prepare slide plates having through-holes with different diameters and to manually remove and replace slide plates having selected through-holes one by one. Therefore, operation becomes complex and this prevents measurement from being quickly performed.

SUMMARY OF THE INVENTION

It is an object of the present invention to provide a particle measuring apparatus and a particle measuring method using the electrical-resistance-change detection method while simplifying the replacement of slide plates and having a high measurement accuracy.

The particle measuring apparatus of the present invention comprises a slide plate movably set between two sample vessels and having through-holes connecting these vessels and a pair of electrodes arranged in both vessels and capable of contact with a sample suspension to be transferred to the sample vessels in order to measure the electrical impedance generated when the sample suspension passes through one of the through-holes by these electrodes and measure particles in the sample suspension in accordance with the electrical impedance; wherein the through-holes on the slide plate are formed by a group of optional through-holes with different diameters.

PREFERRED EMBODIMENTS OF THE INVENTION

According to the present invention, it is also possible to use a structure in which the through-holes are almost concentrically arranged on the slide plate so that a through hole having appropriate diameter can be selected by being rotated from the outside. Moreover, it is possible to use a structure in which the through-holes are primarily arranged in one axial direction on a slide plate so that they can be selected by being moved in one axial direction from the outside.

The diameter of the through-holes is varied depending upon the object of the measurement. In the measurement of blood cells for example, it is preferably 50 μm to 3 mm.

It is preferable that the slide plate has two to twelve through-holes, each having different diameter, more preferably, the number of through-holes is four to six.

Possibly, a plurality of plates having through-holes different in minimum and/or maximum diameter from each other are preferred and can be selected in accordance with the size of particles in the sample suspension by being attached and detached from the outside.

It is preferable that each through-hole bored portion on the slide plate has a tapered plane expanding outward at both ends of the hole. Thereby, an advantage is obtained that electric fields are prevented from excessively concentrating on the margin of a through-hole. In this case, the tapered plane includes C plane shaded so that the cross section becomes a straight line, R plane shaped so that the cross section becomes a curve, or paraboloid.

It is preferable that at least the through-hole bored portion on the slide plate is made of a stiff material such as ruby, sapphire or ceramic. Thereby, advantages are obtained that smooth boring can be made and through-holes can be bored accurately. It is possible to form the whole slide plate with the above materials or form only the through-hole bore portion with the above material.

It is preferable that the slide plate is provided with a protrusion adhering to a sample vessel and that the through-hole is bored at the protrusion. Thereby, advantages are obtained that the contact area between the slide plate and the sample vessel decreases and reduced friction and abrasion at the time of sliding.

The particle measuring method of the present invention comprises a first measurement step for passing a sample suspension through a first through-hole bored on a slide plate set between two sample vessels, measuring the electrical impedance generated when the sample suspension passes through the first through-hole, and measuring particles in the sample suspension in accordance with a change of the electrical impedance and, a second measurement step for passing the sample suspension through a second through-hole bored on the slide plate, measuring the electrical impedance when the sample suspension passes through the second through-hole, and measuring particles in the sample suspension in accordance with a change of the electrical impedance; further comprising a through-hole selection and change step for changing the passages of the sample suspension from the first through-hole to the second through-hole by selecting one through-hole out of a group of through-holes having a diameter different from that of the first through-hole as a second through-hole by sliding the slide plate, between the first measurement process and the second measurement step.

In the case of the particle measuring method, it is preferable that this second through-hole selected in the second measurement step has a diameter smaller than that of the first through-hole. Thereby, an advantage is obtained that large to small particles can be measured in steps one by one.

It is preferable to use a blood sample as the sample suspension and measure blood cells in the blood sample.

To measure particles by the particle measuring apparatus of the present invention, first, a sample suspension is passed through a first through-hole bored on a slide plate set between two sample vessels to measure the electrical impedance generated when the sample suspension passes through the first through-hole and determine particles in the sample suspension in accordance with a change of the electrical impedance (first measurement step). Then, the passages of the sample suspension are changed from the first through-hole to a second through-hole by selecting one through-hole with a diameter different from that of the first through-hole from a group Of through-holes as the second through-hole in accordance with the measurement result in the first measurement step and sliding the slide plate (through-hole selection and change step).

Then, the electrical impedance when the sample suspension passes through the second through-hole bored on the slide plate is determined and particles in the sample suspension are measured in accordance with a change of the electrical impedance (second measurement step). By setting the through-hole selection and change process so that the second through-hole has a diameter smaller than that of the first through-hole, it is possible to quickly measure particles having a wide particle distribution.

The particle measuring apparatus of the present invention makes it possible to easily change through-holes and quickly measure a particle distribution covering a wide range by rotating the slide plate from the outside or moving them in one axial direction from the outside.

When each through-hole bored portion on a slide plate has a tapered plane expanding outward at both ends of the hole, excessive concentration of electric fields is prevented and the measurement accuracy improved.

Moreover, by forming at least the through-hole bored portion on the slide plate with ruby, sapphire, or ceramic, a through-hole can be bored accurately. Furthermore, by constituting the slide plate so that it is provided with a protrusion adhering to a sample vessel and a through-hole bored at the protrusion, the contact area between the slide plate and the sample vessel decreases and the friction and abrasion at the time of sliding are decreased.

DESCRIPTION OF THE PREFERRED EMBODIMENTS

Embodiment 1

Figure 1:
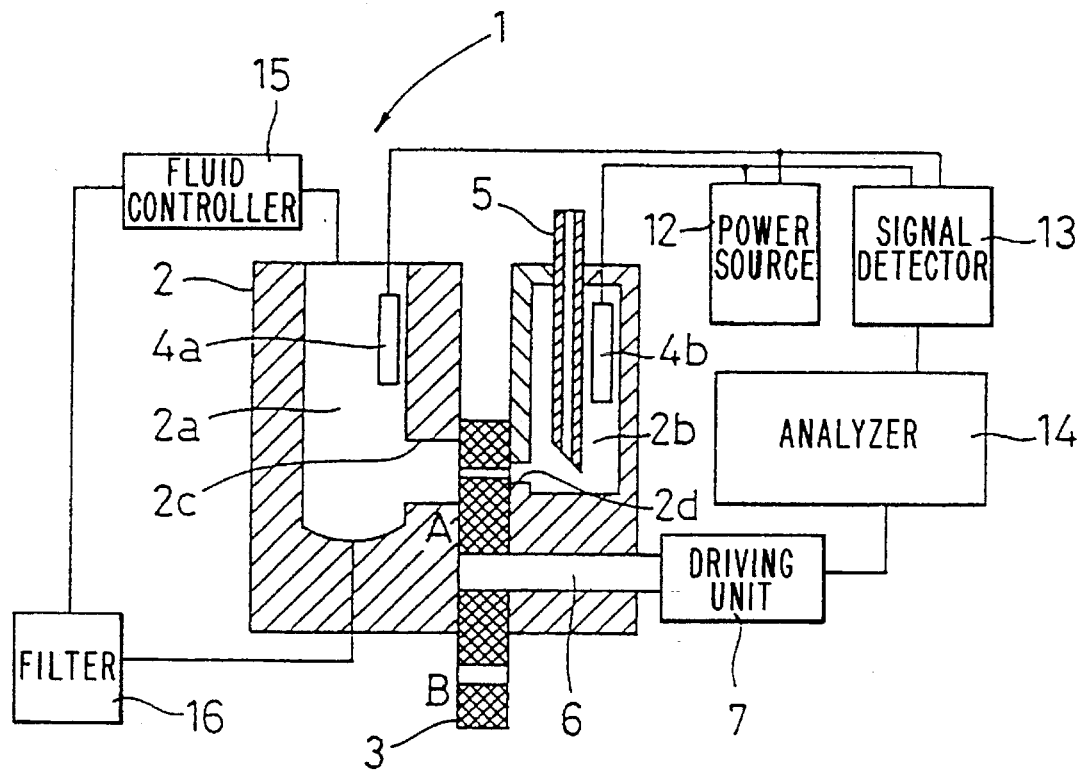
FIG. 1 is a schematic block diagram of the particle measuring apparatus of an embodiment of the present invention.

FIG. 1 shows the particle measuring apparatus of an embodiment of the present invention. The particle measuring apparatus 1 comprises mainly sample vessel 2 and slide plate 3. Sample vessel 2 comprises two tanks 2a and 2b and connective holes 2c and 2d faced each other are bored at the bottom of tanks 2a and 2b respectively. Moreover, a pair of electrodes 4 comprising pole plates 4a and 4b are arranged in tanks 2a and 2b respectively. Furthermore, a sample suction pipe 5 is inserted into tank 2b.

Figure 2:
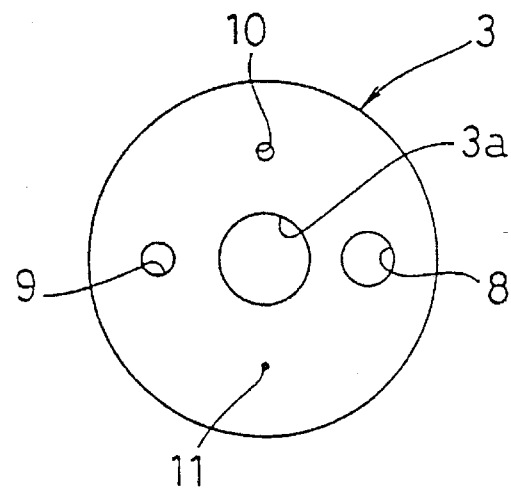
FIG. 2 is a front view of a slide plate of the particle measuring apparatus as shown by FIG. 1.

Slide plate 3, as shown in FIG. 2, is a disk made of ruby or ceramic with an outside diameter of 40 mm and a thickness of 5 mm and driving unit 7 is attached to central hole 3a through driving shaft 6. Driving unit 7 uses a motor such as a stepping motor or DC motor. Four through-holes 8 to 11 each having different diameters are concentrically arranged on slide plate 3 at almost equal intervals. Through-hole 8 has a diameter of 3 mm and a particle measuring area of 150 to 1,200 μm, through-hole 9 has a diameter of 800 μm, and a particle measuring area of 40 to 320 μm, through-hole 10 has a diameter of 200 μm and a particle measuring area of 10 to 80 μm, through-hole 11 has a diameter of 50 μm and a particle measuring area of 2.5 to 20 μm.

slide plate 3 is movably arranged between tanks 2a and 2b so that through-holes 8 to 11 correspond to connective holes 2c and 2d. Thereby, tanks 2a and 2b connect with each other due to movement of slide plate 3 by driving unit 7, when through-holes 8 to 11 are located at positions corresponding to connective holes 2c and 2d.

Pole plates 4a and 4b are connected with power source 12, signal detector 13, and analyzer 14. Moreover, fluid controller 15 for passing a sample filled in sample vessel 2 is connected inside tank 2a. Fluid controller 15 is connected with one end of sample suction pipe 5 and filter 16.

Fluid controller 15 is able to pass a sample filled into sample vessel 2 to tank 2b through sample suction pipe 5 by a not-illustrated control unit and moreover to regulate particle diameters of the sample filled into sample vessel 2 by leading the sample to filter 16 being driven with a not-illustrated control unit.

Moreover, it is possible to form an optional number of through-holes on slide plate 3. When using the above motor rotating at equal rotation angles, it is preferable to form a group of 2 to 12 through-holes with different diameters.

Figure 3:
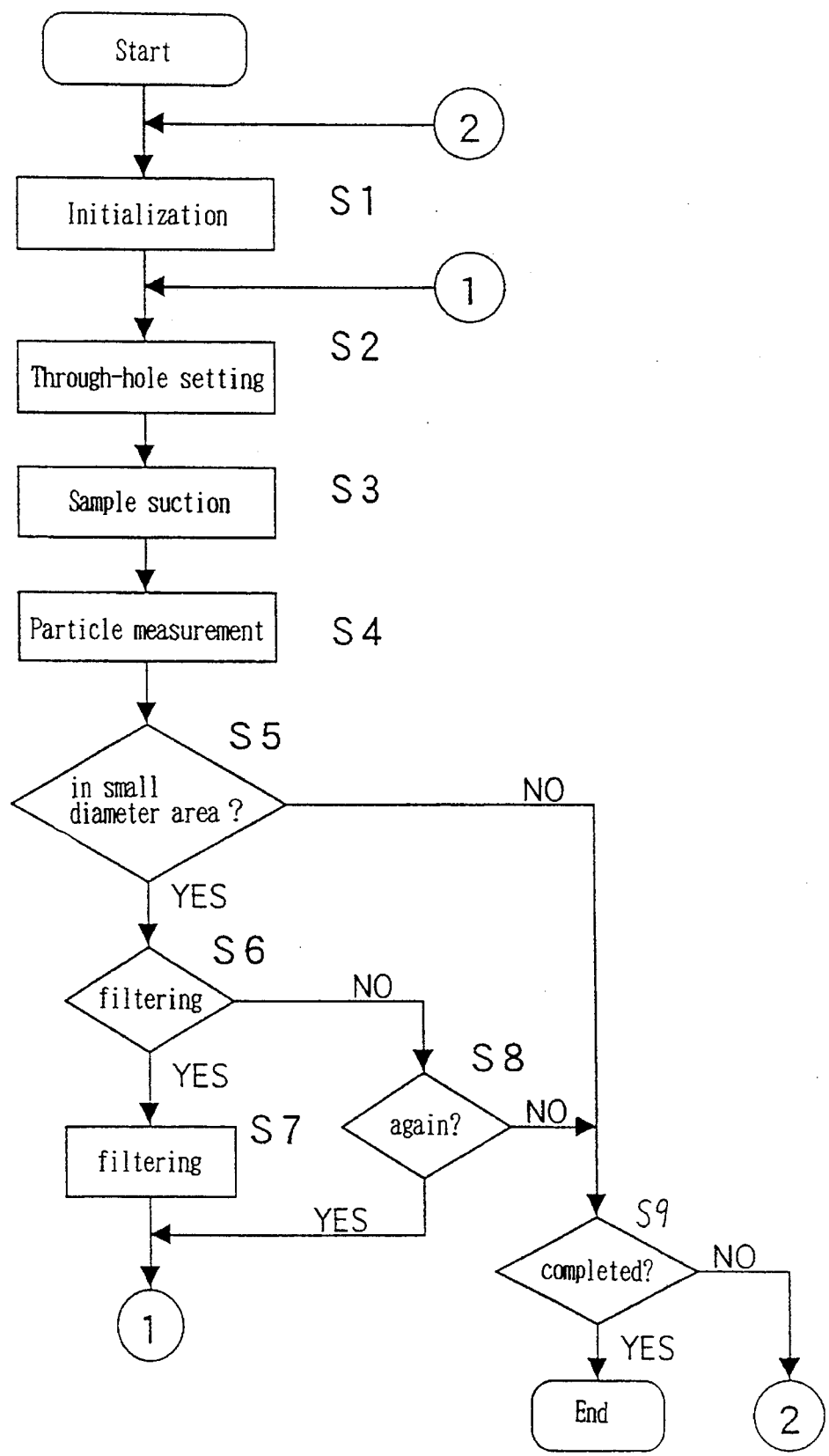
FIG. 3 is a flow chart showing a measuring method of an embodiment of the present invention.

Particle measuring apparatus 1 of this embodiment performs measurement in accordance with the following operation. FIG. 3 is a flow chart showing the measuring procedure. First, initialization is performed in step S1. Then, one of the through-holes 8 to 11 corresponding to the particle diameter of a sample to be measured is selected in step S2 and the through-hole is moved to a position corresponding to connective holes 2c and 2d. In this case, through-hole 8 (diameter of 300 μm) is selected which has the largest diameter among through-holes 8 to 11.

It is possible to use a generally known means as the setting means for correctly setting one of the through-holes 8 to 11 to a predetermined position and the detection means for detecting the setting position. For example, a through-hole can be set to a correct position by detecting the home position of slide plate 3 by combining a contact member with a microswitch and reading the rotation angle of slide plate 3 by the number of steps of the motor serving as driving unit 7 (in the case of a stepping motor) or reading the rotation angle by a rotary encoder connected to the motor.

Next, in step S3, a suspension sample of approx. 10 ml to be measured is filled into sample vessel 2, then the sample is passed into tank 2b through sample suction pipe 5 by driving fluid controller 15. Thereby, the sample passes through through-hole 8. The sample passed into tank 2b is discharged outside the system from sample suction pipe 5.

Figure 4:
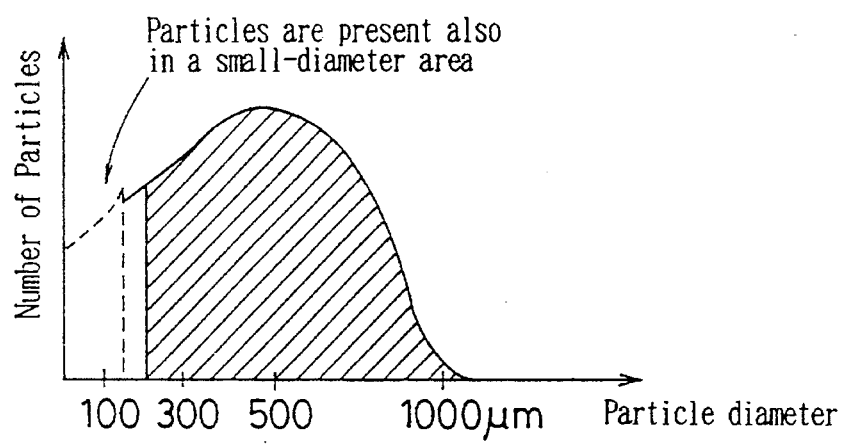
FIG. 4 is a graph showing an example of a measurement and analysis result of a particle distribution obtained by the measuring method in FIG. 3.

In step S4, particles of the sample passing through through-hole 8 are measured and analyzed. A particle distribution is measured and analyzed by analyzer 14 by assuming the number of particles as the number of pulses and the volume of a particle as the pulse height. The result of measuring and analyzing the particle distribution using through-hole 8 is displayed on a screen in the form of a graph as shown in FIG. 4. (From this analysis result, it is estimated that particles with a particle diameter of approx. 150 μm or less are also present.)

Then, in step S5, the operator decides whether a particle with a diameter of 300 μm or less is measured in accordance with the measurement result of the particle distribution in step S4. When a particle with a diameter of 300 μm or less is measured, the step shifts from S5 to S6 and the operator decides whether or not to filter the sample. To filter the sample, the sample is filtered in step S7. When filtering of the sample is completed, the step shifts from S7 to S2 and slide plate 3 is rotated so that a through-hole with a smaller diameter can be set. In this case, through-hole 8 is changed to through-hole 9. Hereafter, measurement is continued in the same manner to successively set a through-hole with a smaller diameter.

Figure 5:
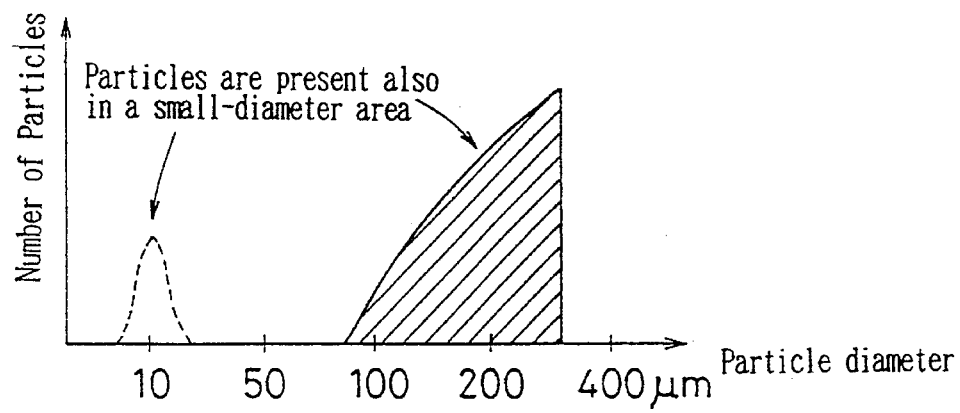
FIG. 5 is a graph showing an example of a measurement and analysis result of a particle distribution obtained by the measuring method in FIG. 3.
Figure 6:
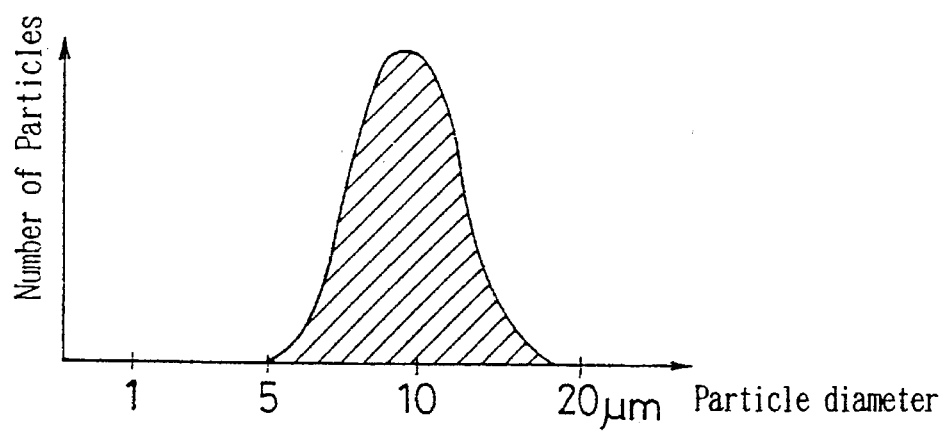
FIG. 6 is a graph showing an example of a measurement and analysis result of a particle distribution obtained by the measuring method in FIG. 3.
Figure 7:
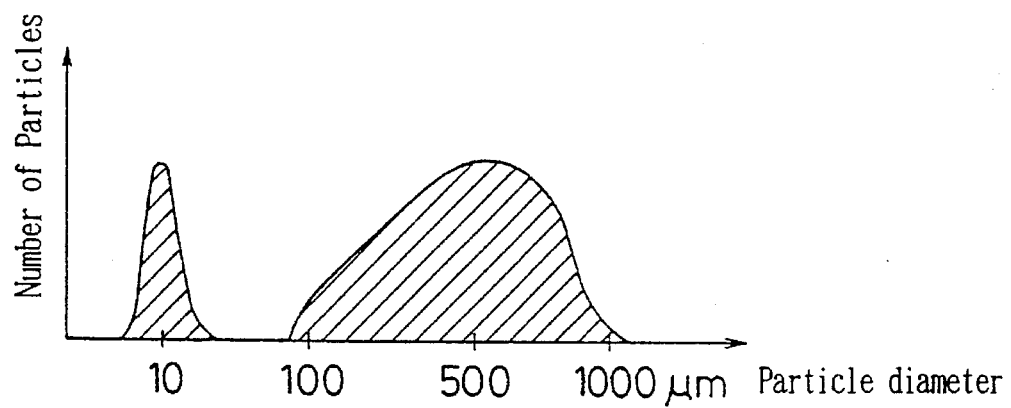
FIG. 7 is a graph showing an example of a measurement and analysis result of a particle distribution obtained by the measuring method in FIG. 3.
Figure 8:
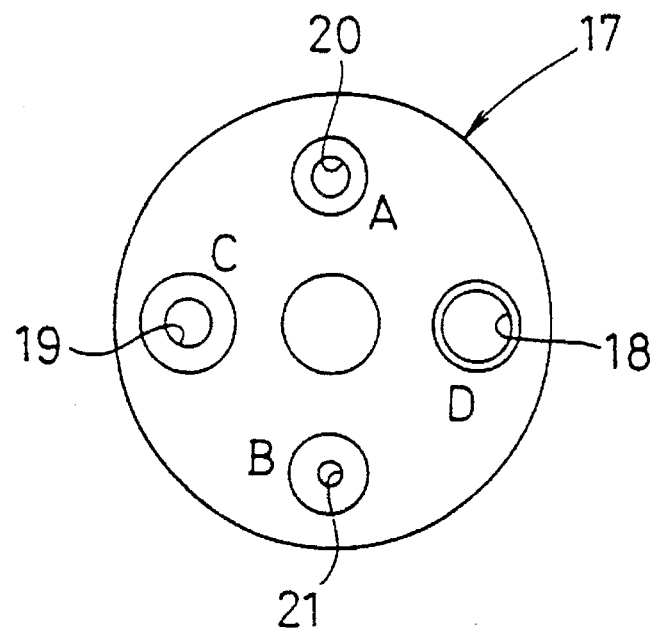
FIG. 8 is a front view showing another embodiment of the slide plate of the particle measuring apparatus.
Figure 9:
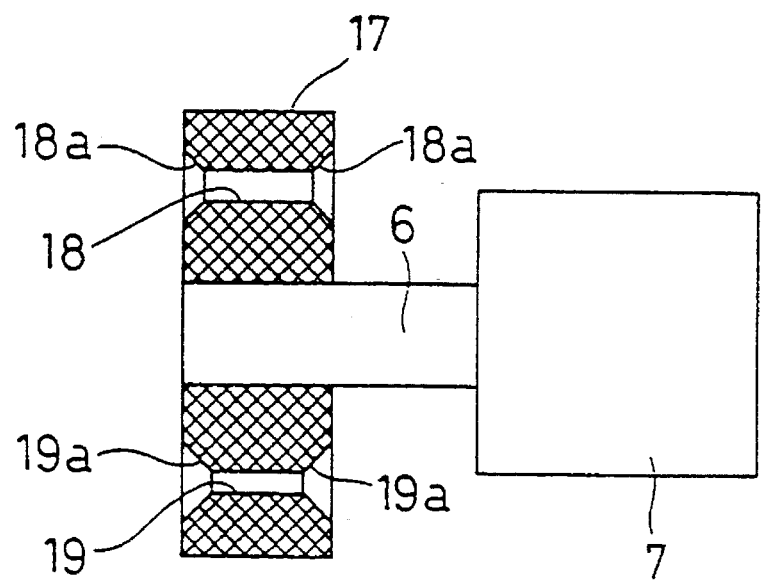
FIG. 9 is a side view of the slide plate in FIG. 8.

When the operator decides in S6, not to filter the sample, the step shifts from S6 to S8. In step S8, it is decided whether to measure the sample again without filtering the sample. When the decision in step S8 is YES, the step shifts to S2. Moreover, when no particle with a diameter of 300 μm or less is detected from the particle measurement result in step S4 and the decision in step S8 is NO, the step shifts to S9 and the operator decides whether or not to complete the measurement. When the operator decides to complete the measurement, sample vessel 2 is washed and the measurement is completed. When continuing measurement of the sample, the step shifts from S9 to S1. FIGS. 5 to 7 show the particle diameter measurement results obtained from the above measurement by setting the through-holes 9 to 11 respectively.

Embodiment 2

Figure 10:
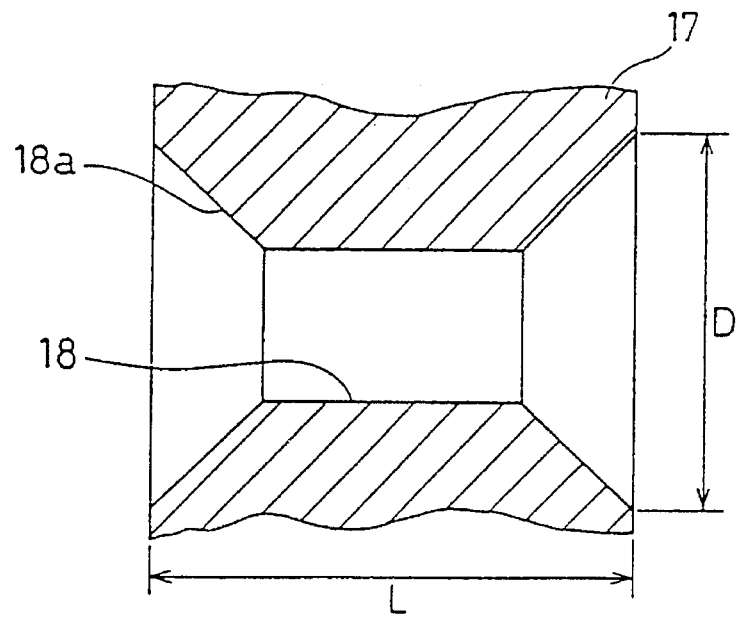
FIG. 10 is a partially enlarged view of FIG. 9.
Figure 11:
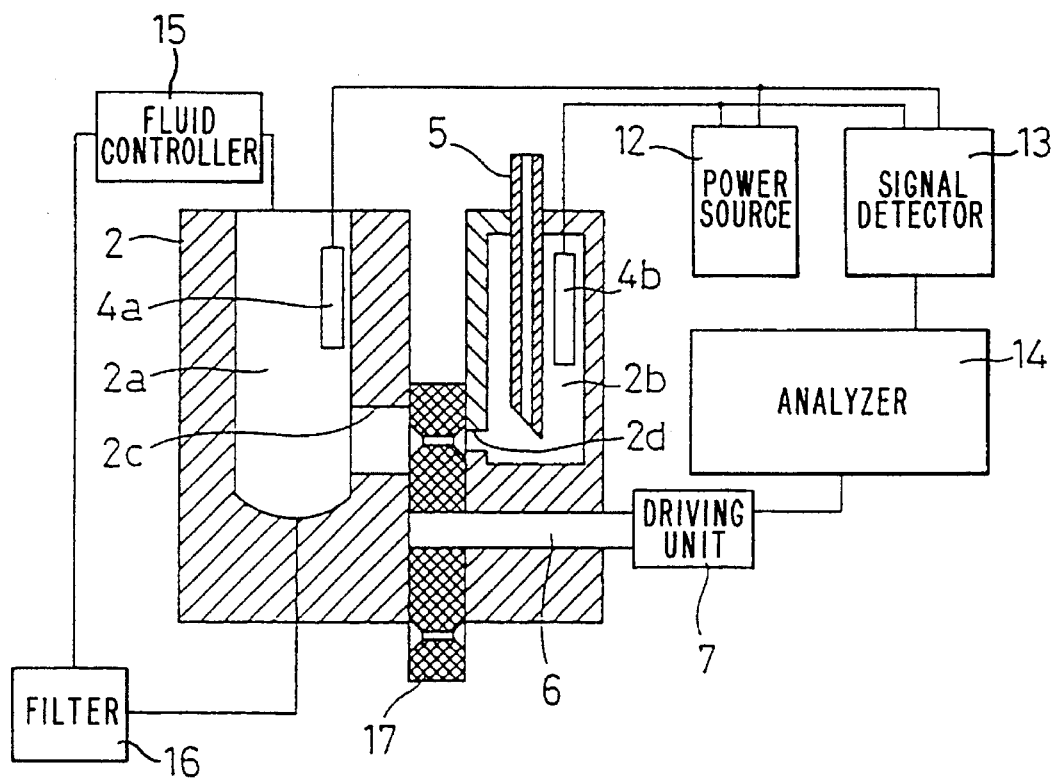
FIG. 11 is a schematic block diagram of a particle measuring apparatus using the slide plate in FIG. 8.

In the case of embodiment 1, through-holes 8 to 11 on slide plate 3 are bored with constant diameter through slide plate 3 for each through-hole bored portion. However, as shown in FIGS. 8 to 11, it is also possible to form tapered planes 18a to 21a expanding outward at both ends of through-holes 18 to 21 respectively. In this case, tapered planes 18a to 21a are C planes, that is, planes whose cross section is shaped with a straight line having the same tilt angle which is preferred to be a tilt angle of 30° to 60° and most preferred to be 45°. It is also possible to form tapered planes 18a to 21a by R plane, that is, a plane whose cross section is shaped with a curve. In this case, it is preferable to set the radius of curvature of the R plane to 10 to 50 μm though it depends on the through-hole diameter. Moreover, as shown in FIG. 10, it is preferable to form the R plane so that the ratio of diameter to through-hole length D/L comes to 1/1.2 to 1/1.4. In this case, however, if the ratio D/L is too large, an electric field at the opening of the hole is unevenly formed and the proportional relation between particle volume and pulse height is not effected. On the contrary, if the ratio D/L is too small, there occurs a problem when a plurality of particles enter the through-hole.

Embodiment 3

Figure 12:
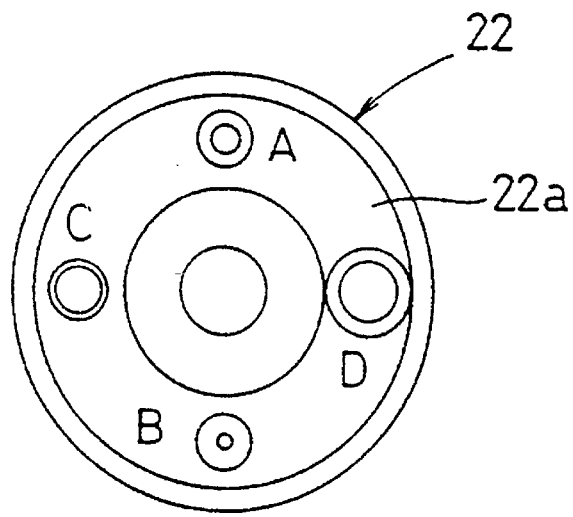
FIG. 12 is a front view showing a slide plate of a particle measuring apparatus as another embodiment of the present invention.
Figure 13:
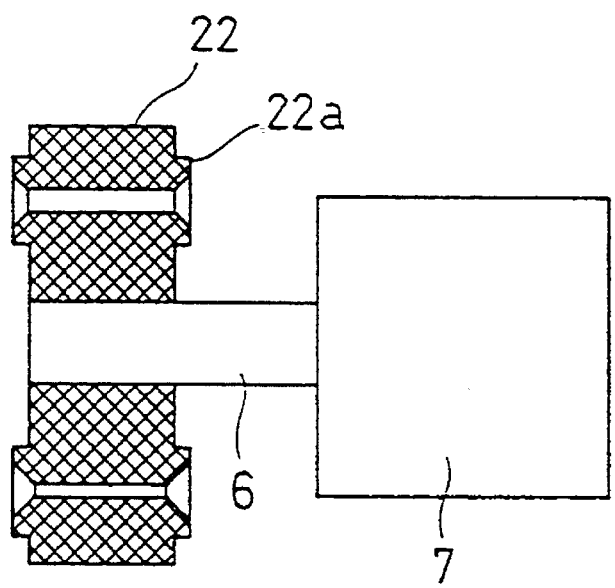
FIG. 13 is a side view of the slide plate in FIG. 12.

In the case of embodiment 1, the bored plane of through-holes 8 to 11 on slide plate 3 are formed flat. However, as shown in FIGS. 12 and 13, it is also possible to form protrusion 22a on the main surface of slide plate 22 around the through-hole opening. In this case, protrusion 22a becomes annular. Thereby, it is possible to decrease the friction and abrasion at the time of sliding by decreasing the contact area between slide plate 3 and sample vessel 2. Furthermore, it is preferable to set the height of protrusion 22a to about 0.1 to 1 mm.

Embodiment 4

Figure 14:
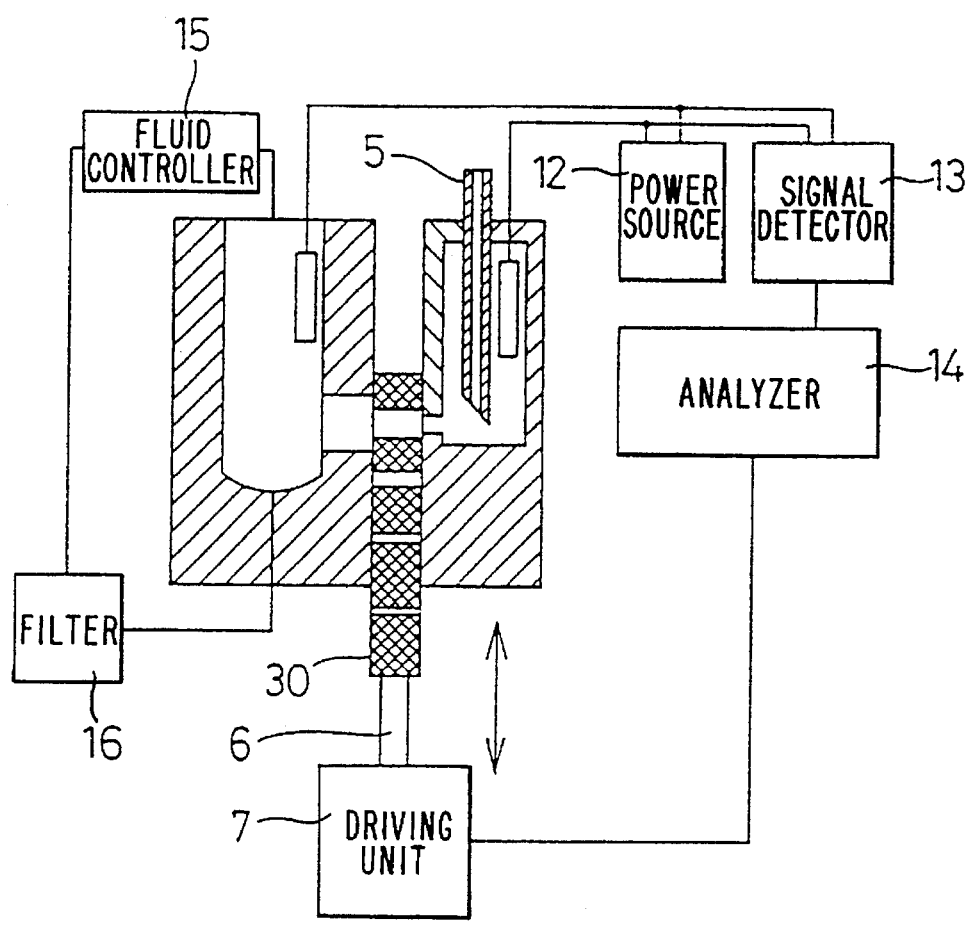
FIG. 14 is a schematic block diagram showing the particle measuring apparatus as still another embodiment of the present invention.
Figure 15:
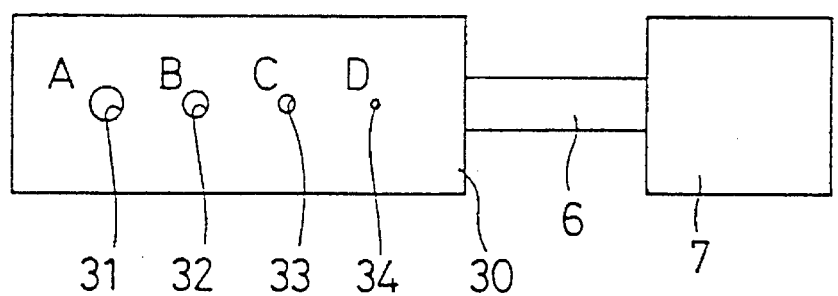
FIG. 15 is a front view of the slide plate of the particle measuring apparatus in FIG. 14.
Figure 16:
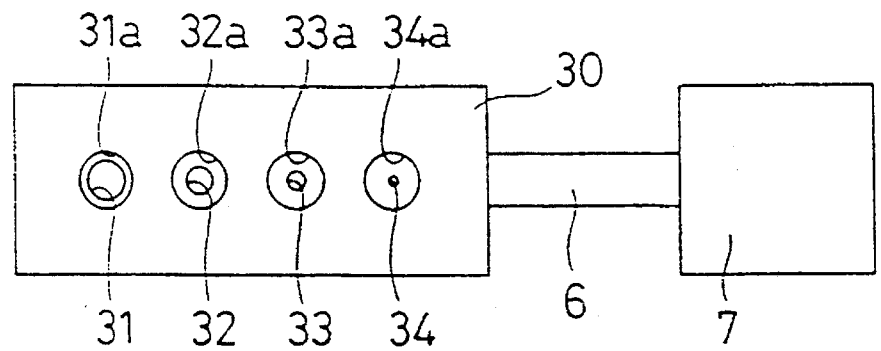
FIG. 16 is a front view showing another embodiment of the slide plate in accordance with the present invention.

Embodiment 1 is constituted so that a through-hole can be selected by rotating slide plate 3 from the outside. However, as shown in FIGS. 14 and 15, it is also possible to use a structure in which through-holes 31 to 34 can be selected by forming slide plate 30 into a rectangle, and linearly arranging through-holes 31 to 34 on slide plate 30 primarily in one axial direction, and moving plate 30 in one axial direction from the outside. Here, the thorough-holes are formed in the longitudinal direction of slide plate 30 in order of size of diameters. A driving unit for moving slide plate 30 in one axial direction can be constituted by connecting a ball screw to the rotary shaft of a DC motor through a coupling and connecting shaft 10 to a moving plate engaged with the ball screw (not illustrated). This structure makes it possible to measure and analyze the particle distribution of a sample in accordance with the measurement procedure described in embodiment 1.

Figure 17:
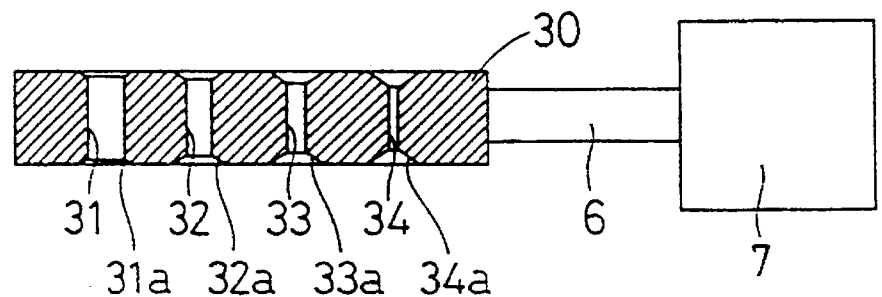
FIG. 17 is a side view of the slide plate in FIG. 16.
Figure 18:
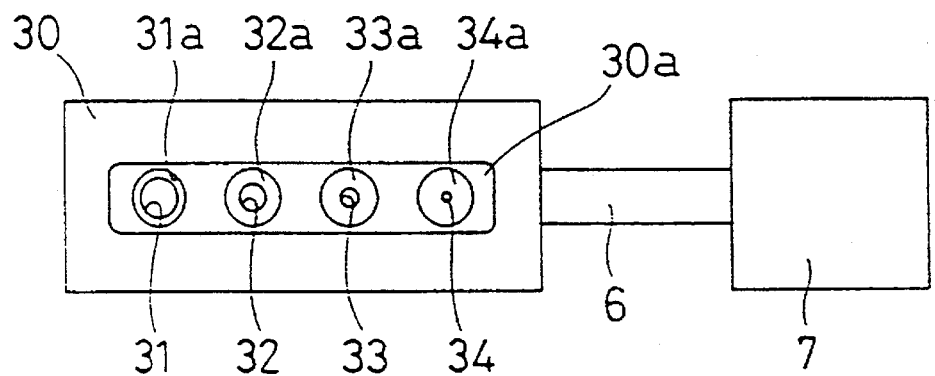
FIG. 18 is a front view showing still another embodiment of the slide plate corresponding to FIG. 16.
Figure 19:
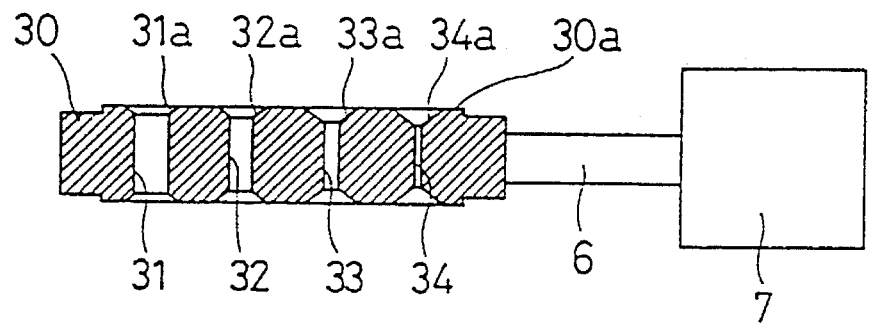
FIG. 19 is a side view of the slide plate in FIG. 18.

As shown in FIGS. 17 and 18, it is also possible to form tapered planes 31a to 34a (C plane or R plane) expanding outward at both ends of the opening of through-holes 31 to 34 on slide plate 30. In this case, tapered planes 31a to 34a are formed by C plane with a tilt angle of approx. 45° so that the ratio D/L comes to 1/1.2 to 1/1.4 similarly to the above. Thereby, electric fields are prevented from extreme concentration on the margins of the opening of through-holes 8 to 11.

Moreover, it is possible to form consecutive linear protrusions 30a around the opening of through-holes 31 to 34 on the main surface of slide plate 30. Thereby, it is possible to decrease friction and abrasion at the time of sliding by reducing the contact area between slide plate 30 and sample vessel 2.

Embodiment 5

Figure 20:
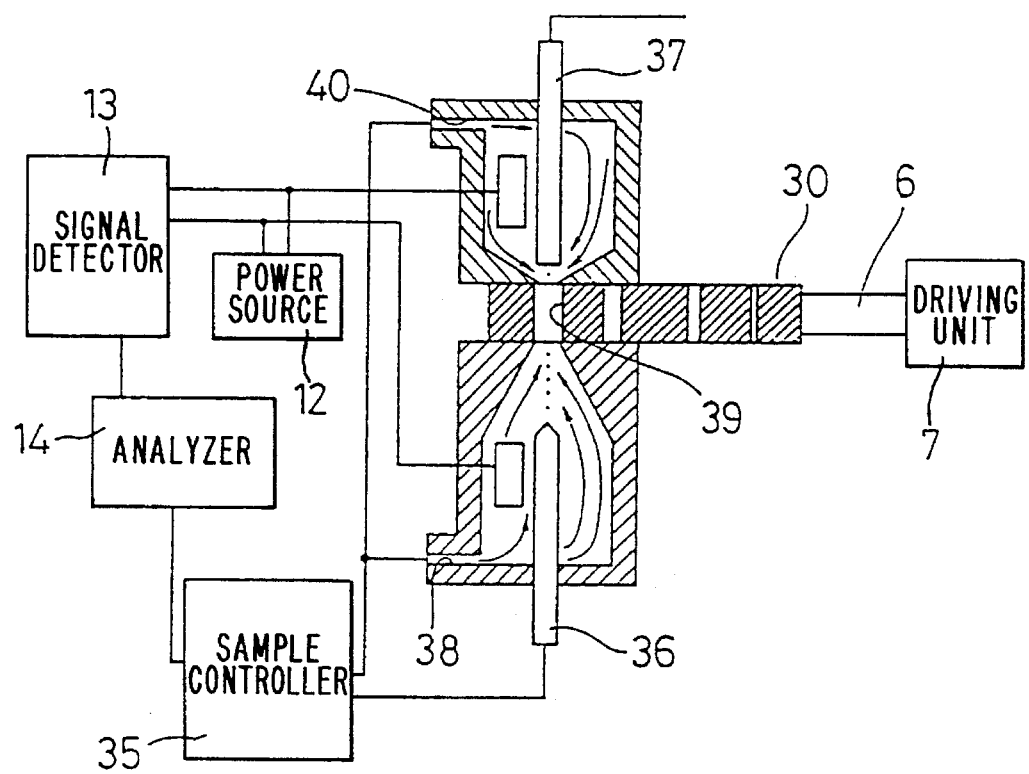
FIG. 20 is a schematic block diagram of the particle measuring apparatus of still another embodiment of the present invention.

In the case of embodiment 1, the movement of a sample is assumed to be almost horizontal. However, FIG. 20 shows a structure of a particle measuring apparatus using the so-called electrical-resistance-change detection method of the sheath flow system in which measurement particles are covered with a particle-free liquid called a sheath liquid and thereafter aligned by using a hydrodynamic focusing and measured.

The existing electrical-resistance-change detection method has disadvantages in that a difference occurs between the intensities of detection signals depending on the position in a through-hole when a particle is passing through, two or more particles adjacently passing through a through-hole are judged as one particle, or the velocity of particles suddenly decreases after passing through a through-hole or noises are generated by the fact that particles passing through a through-hole stagnate around a through-holes, problems caused by neighboring passage of sample particles through a through-hole. This embodiment is constituted so as to control the neighboring passage of sample particles through a through-hole by using the sheath flow system.

A suspension sample prepared by sample controller 35 is discharged from sample nozzle 36, passes through through-hole 39, and is collected with sample suction pipe 37. In the case of the sheath flow method, the sheath liquid comes in from front sheath intake port 38 and moves in a manner to enclose sample nozzle 36.

The suspension sample discharged from sample nozzle 36 is slowly focused while being enclosed with the front sheath liquid and particles of the suspension sample are aligned when passing through through-hole 39. Moreover, a back sheath liquid for enclosing the particles passing through through-hole 39 and leading them to sample suction pipe 37 is introduced from back sheath liquid intake port 40. Thereby, it is possible to reduce the problem that the particle passing through through-hole 39 stagnates around through-hole 39 due to the sudden decrease of velocity.

Embodiment 6

Figure 21:
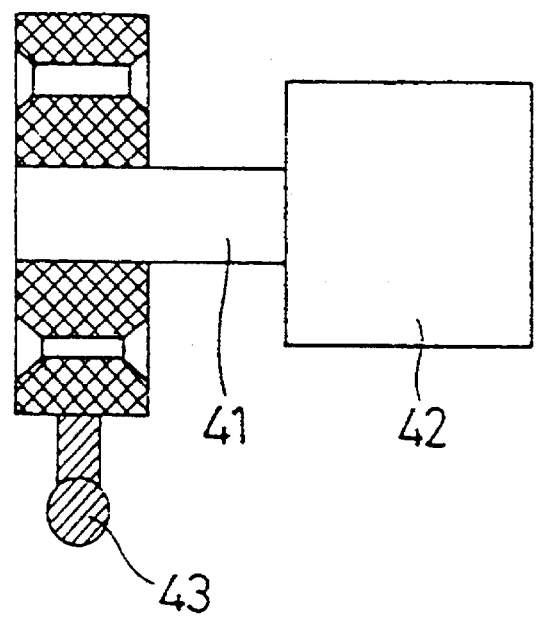
FIG. 21 is a front sectional view of the slide plate of still another embodiment of the present invention.
Figure 22:
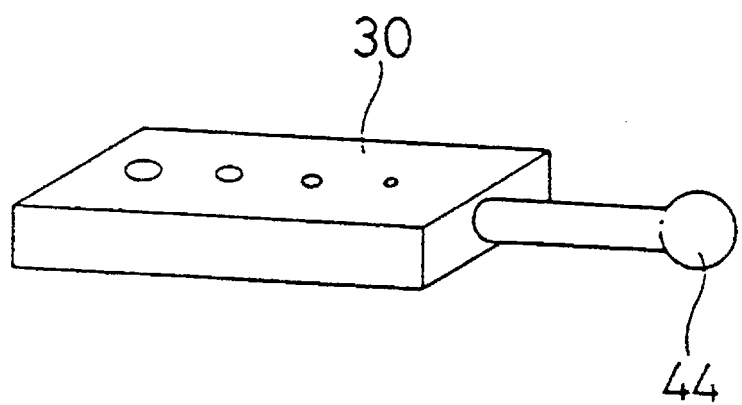
FIG. 22 is a perspective view of the slide plate of still another embodiment of the present invention.

In the case of the above mentioned embodiments 1 to 5, a structure is shown in which a slide plate is moved by a driving unit. In the case of this embodiment, however, a structure in which a through-hole can be selected by manually moving the slide plate is shown in FIGS. 21 and 22. In FIG. 21, slide plate 45 is rotatably supported by bearing 42 through shaft 41 and moreover, a handle for the operator to manually rotate slide plate 45 is formed.

In FIG. 22, handle 44 is formed on slide plate 46. Thereby, an operator can set optional through-holes to a measuring position one by one by rotating handle 43 or moving handle 44 in one axial direction.

It is possible to adjust the position of a through-hole while monitoring the information for through-hole position by using, for example, an encoder for rotation or linear movement. Moreover, it is possible to reliably perform the positioning of a through-hole by combining a ball plunger having an energized ball with a recess for holding the ball.

In these embodiments, through-holes can be changed successively by rotating a slide plate from the outside or moving it in one axial direction. Therefore, it is possible to quickly and easily set a through-hole to a measuring position. These embodiments are particularly effective for measurements in which particle distribution covers a wide range.

ADVANTAGES OF THE INVENTION

The present invention makes it possible to quickly and easily set a through-hole to a measuring position because through-holes on a slide plate are formed by a group of plural optional through-holes with different diameters.

Moreover, the present invention makes it possible to quickly and easily set a through-hole to a measuring position because through-holes are almost concentrically arranged on a slide plate and they can be selected by rotating the slide plate from the outside.

Furthermore, the present invention makes it possible to quickly and easily set a through-hole to a measuring position because through-holes are arranged primarily in one axial direction on a slide plate and they can be selected by moving the slide plate in one axial direction from the outside.

Furthermore, the present invention makes it possible to obtain a high measurement accuracy because each through-hole bored portion of the slide plate has a tapered plane expanding outward at both ends of each hole opening and thereby an electric field is evenly formed at both opening ends of a through-hole.

Furthermore, the present invention makes it possible to smoothly bore a hole and obtain a high measurement accuracy because at least the through-hole bored portion on a slide plate is made of ruby, sapphire or ceramic.

Furthermore, the present invention makes it possible to decrease the contact area between a slide plate and a sample vessel and decrease the friction and abrasion at the time of sliding because the slide plate has a protrusion adhering to the sample vessel and a through-hole is formed at the protrusion. Therefore, it is possible to keep a high measurement accuracy for a long time.

Furthermore, the present invention makes it possible to quickly and easily set a through-hole to a measuring position by providing a through-hole selection and change process for selecting a through-hole out of a group of through-holes having a diameter different from that of a first through-hole as a second through-hole based on the measurement result of a first measurement process and changing the passage of a sample suspension from the first through-hole to the second through-hole by sliding a slide plate between the first and second measurement processes.

Furthermore, the present invention makes it possible to simplify the operation for changing through-holes stepwise one by one correspondingly to particle distribution and Hick measurement because the second through-hole selected in a second measurement process has a diameter smaller than that of the first through-hole.

What is claimed is:

1. A particle measuring apparatus, comprising:

a first sample vessel;

a second sample vessel;

a slide plate having at least one first through-hole having a first diameter and at least one second through-hole having a second diameter, said slide plate being selectively movable at least between a first position connecting said first and second sample vessels through said at least one first through-hole and a second position connecting said first and second sample vessels through said at least one second through-hole; and electrodes arranged in said first and second sample vessels, said electrodes contacting with a sample suspension in said first and second sample vessels to measure an electrical impedance generated when the sample suspension passes through selected one of said first and second through-holes and to measure particles in the sample suspension based on the detected electrical impedance.

2. The particle measuring apparatus according to claim 1, wherein said first and second through-holes are arranged almost concentrically on said slide plate and either one of said first and second positions can be selected by rotating said slide plate.

3. The particle measuring apparatus according to claim 2, wherein said slide plate is rotated by an actuator.

4. The particle measuring apparatus according to claim 2, wherein said slide plate is rotated manually.

5. The particle measuring apparatus according to claim 1, wherein said first and second through-holes are arranged on said slide plate primarily in an axial direction thereof so that at least one of said first and second positions can be selected by moving said slide plate along said axial direction.

6. The particle measuring apparatus according to claim 5, wherein said slide plate is moved by an actuator.

7. The particle measuring apparatus according to claim 5, wherein said slide plate is moved manually.

8. The particle measuring apparatus according to claim 1, wherein said slide plate has between two to twelve through-holes, each of said two to twelve through-holes having a different diameter.

9. The particle measuring apparatus according to claim 1, wherein at least one of said first and second through-holes is provided with a tapered portion expanding outwardly at both ends thereof.

10. The particle measuring apparatus according to claim 1, wherein at least portion of said slide plate where said first and said second through-holes are formed is made of a stiff material.

11. The particle measuring apparatus according to claim 1, wherein said first sample vessel includes a first connective hole, said second sample vessel includes a second connective hole, and said slide plate has a protrusion opposing at least one of said first and second connective holes and said first and second through-holes are formed at said protrusion.

12. A particle measuring apparatus, comprising:

a first sample vessel;

a second sample vessel;

a slide plate having at least one first through-hole having a first diameter and at least one second through-hole having a second diameter, said slide plate being selectively movable at least between a first position connecting said first and second sample vessels through said at least one first through-hole and a second position connecting said first and second sample vessels through said at least one second through-hole; and electrodes arranged in said first and second sample vessels, said electrodes contacting with a sample suspension in said first and second sample vessels to measure an electrical impedance generated when the sample suspension passes through selected one of the through-holes and to measure particles in the sample suspension based on the detected electrical impedance; wherein said slide plate includes a plurality of plates, one of said plurality, of plates having said first and second through-holes and another of said plurality of plates having through-holes different in diameter from said first and second through-holes, one of said plurality of plates can be selected in accordance with the size of particles in the sample suspension by attaching and detaching said plates from outside.

* * * * *